United States Patent
Mauclaire

(10) Patent No.: US 11,628,043 B2
(45) Date of Patent: Apr. 18, 2023

(54) DENTAL APPLIANCE FOR CONSTRAINING THE TONGUE

(75) Inventor: Claude Mauclaire, Troyes (FR)

(73) Assignee: TONGUE LAB EUROPE

(*) Notice: Subject to any disclaimer, the term of this patent is extended or adjusted under 35 U.S.C. 154(b) by 131 days.

(21) Appl. No.: 12/976,489

(22) Filed: Dec. 22, 2010

(65) Prior Publication Data

US 2011/0284011 A1    Nov. 24, 2011

Related U.S. Application Data

(63) Continuation-in-part of application No. PCT/EP2009/060226, filed on Aug. 6, 2009.
(Continued)

(30) Foreign Application Priority Data

Aug. 6, 2008 (FR) ...................................... 0855452

(51) Int. Cl.
*A61C 7/00* (2006.01)
*A61F 5/56* (2006.01)

(52) U.S. Cl.
CPC ................. *A61C 7/00* (2013.01); *A61F 5/566* (2013.01)

(58) Field of Classification Search
CPC .......... A61F 5/566; A61F 5/56; A61F 5/0006; A61F 5/0003; A61F 5/00; A61F 2005/563; A61B 1/24; A61B 17/24; A61C 7/08; A61C 7/10; A61C 7/00; A61C 7/145; A61C 7/20; A61C 7/30; A61C 7/28; A61C 7/282; A61C 7/285; A61C 7/287; A61C 7/303
(Continued)

(56) References Cited

U.S. PATENT DOCUMENTS 3,132,647 A    5/1964  Corniello
3,162,948 A *  12/1964 Gerber ..................... A61C 7/00
                                                         433/7
(Continued)

FOREIGN PATENT DOCUMENTS

CN    201520868439 U    11/2015
DE      195 03 288       7/1996
(Continued)

OTHER PUBLICATIONS

HOME Stratosphere, "Architectural Types of Arches," https://www.homestratosphere.com/types-of-arches/.*
(Continued)

*Primary Examiner* — Camtu T Nguyen
(74) *Attorney, Agent, or Firm* — Merchant & Gould P.C.

(57) ABSTRACT

A dental appliance and method of treatment are disclosed. The dental appliance attaches to predetermined teeth of an upper jaw of a patient, and includes a constrainment mechanism positioned above a patient's tongue, wherein the constrainment mechanism is shaped to limit movement of a posterior zone of the patient's tongue. The constrainment mechanism allows at least an anterior zone and lateral edges of the patient's tongue to perform movements necessary for speech and swallowing. The method of treatment includes use of the dental appliance to reduce the volume of a patient's tongue and enlarge the airways, and can be combined with use of another dental appliance to correct another aspect of the patient's tongue.

19 Claims, 6 Drawing Sheets

Related U.S. Application Data

(60) Provisional application No. 61/086,684, filed on Aug. 6, 2008.

(58) Field of Classification Search
USPC ........ 602/902; 128/859, 846, 848, 860, 857; 433/140
See application file for complete search history.

(56) References Cited

U.S. PATENT DOCUMENTS

| | | | | |
|---|---|---|---|---|
| 4,471,771 | A | * | 9/1984 | Brown .................. A61F 5/0006 128/859 |
| 4,669,459 | A | | 6/1987 | Spiewak et al. |
| 4,901,737 | A | | 2/1990 | Toone |
| 4,986,283 | A | | 1/1991 | Tepper |
| 5,052,409 | A | * | 10/1991 | Tepper .................... A61F 5/566 128/859 |
| 5,199,872 | A | * | 4/1993 | Leal ......................... A61B 1/24 433/136 |
| 5,376,001 | A | | 12/1994 | Tepper |
| 5,816,800 | A | | 10/1998 | Brehm et al. |
| 5,871,350 | A | | 2/1999 | Clark et al. |
| 6,033,216 | A | | 3/2000 | Souris |
| 6,082,996 | A | | 7/2000 | Haskell |
| 6,467,484 | B1 | | 10/2002 | De Voss |
| 6,766,802 | B1 | * | 7/2004 | Keropian ................ A61F 5/566 128/848 |
| 7,861,722 | B2 | | 1/2011 | Keropian |
| 7,861,724 | B2 | | 1/2011 | Keropian |
| 10,285,782 | B2 | | 5/2019 | Mauclaire |
| 10,772,757 | B1 | * | 9/2020 | Harris ....................... A61F 5/56 |
| 11,033,421 | B1 | * | 6/2021 | Davis ..................... A61F 5/566 |
| 2001/0027793 | A1 | | 10/2001 | Tielmans |
| 2008/0041396 | A1 | * | 2/2008 | Lucker .................... A61F 5/566 128/845 |
| 2009/0126742 | A1 | | 5/2009 | Summer |
| 2011/0262881 | A1 | | 10/2011 | Mauclaire |
| 2012/0247485 | A1 | * | 10/2012 | Timmons ................ A61F 5/566 128/848 |
| 2013/0125902 | A1 | * | 5/2013 | Danielian .............. A61B 17/24 128/859 |
| 2019/0314115 | A1 | | 10/2019 | Mauclaire |

FOREIGN PATENT DOCUMENTS

| | | |
|---|---|---|
| DE | 100 11 687 | 11/2000 |
| JP | 1991042902 U1 | 9/1991 |
| JP | 8-275960 A | 10/1996 |
| JP | 2006-42963 A | 2/2006 |
| JP | 2006507038 A | 3/2006 |
| JP | 2011502715 A | 1/2011 |
| JP | 2014506161 A | 3/2014 |
| WO | 96/11653 A1 | 4/1996 |
| WO | 2005000142 A2 | 1/2005 |
| WO | WO 2006/15216 | 11/2006 |
| WO | 2007002350 A2 | 1/2007 |
| WO | 2007092249 A2 | 8/2007 |
| WO | 2007136551 A2 | 11/2007 |
| WO | WO 2010/015685 A1 | 2/2010 |

OTHER PUBLICATIONS

International Search Report and Written Opinion dated May 14, 2012.

Dentaurum, "Wire appliances, rapid palatal expansion (RPE) appliances: The tongue shield for mesialisation," Feb. 15, 2008, accessed via Internet Archive Wayback Machine at http://www.o-atlas.de/eng/kapitel6_181.php.

International Search Report and Written Opinion for Application No. PCT/EP2009/060226 dated Nov. 13, 2009.

Unitek MIA Quad Helix System, 3M Unitek, 6 pages (1999).

Singh, Dave G., Effects of the Full Breath Solution Appliance for the Treatment of Obstructive Sleep Apnea: A Preliminary Study, The Journal of Craniomandibular Practice, 2009.

Florman et al. "Diagnosing Early Interceptive Orthodontic Problems—Part 2", ADA CERP, 11 pages (Mar. 2008).

Stahl F, Grabowski R, Gaebel M & Kundt G (2007) Relationship between occlusal findings and orofacial myofunctional status in primary and mixed dentition. Part II: Prevalence of orofacial dysfunctions. J. Orofac. Orthop. 68: 74-90 (2007).

Non-Final Office Action for U.S. Appl. No. 16/365,269 dated Jan. 6, 2023.

* cited by examiner

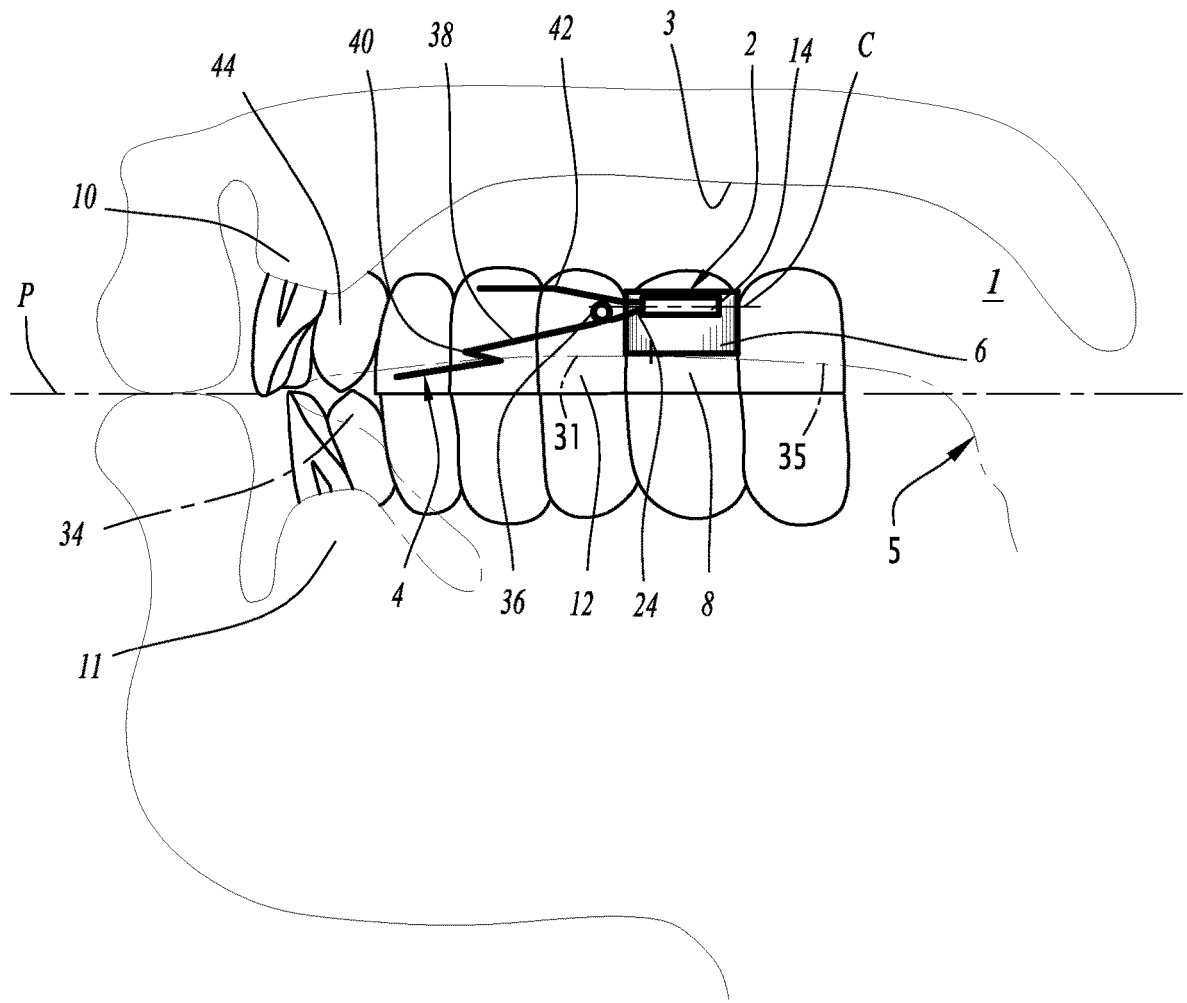
FIG.3
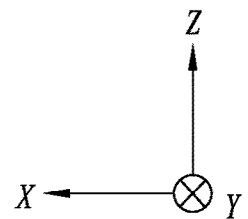

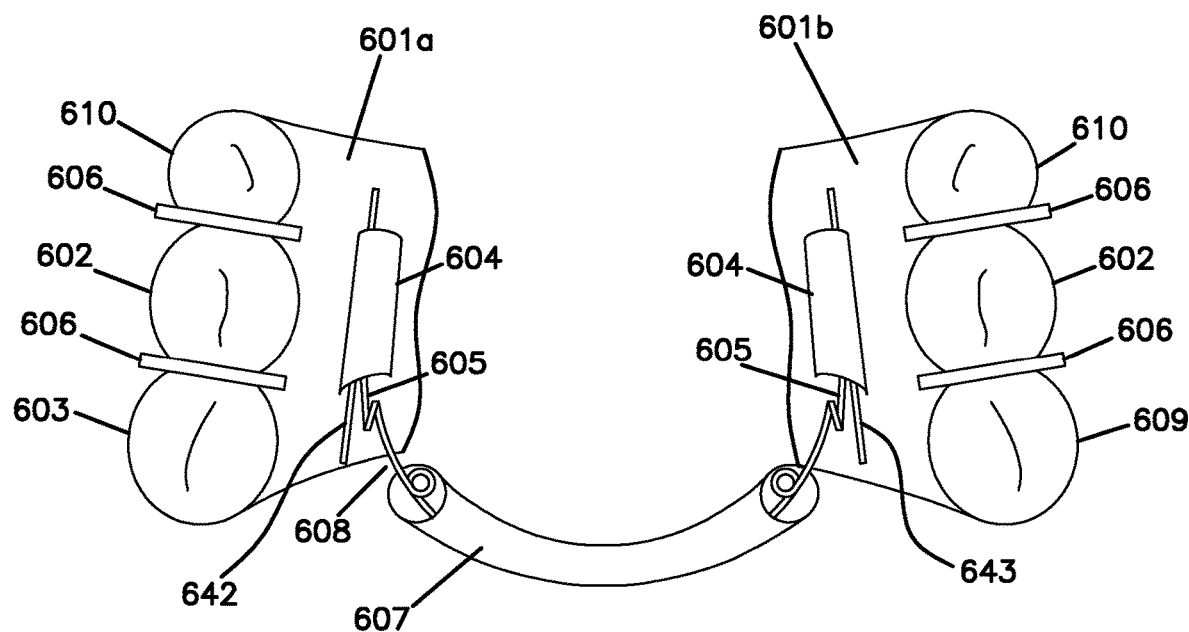
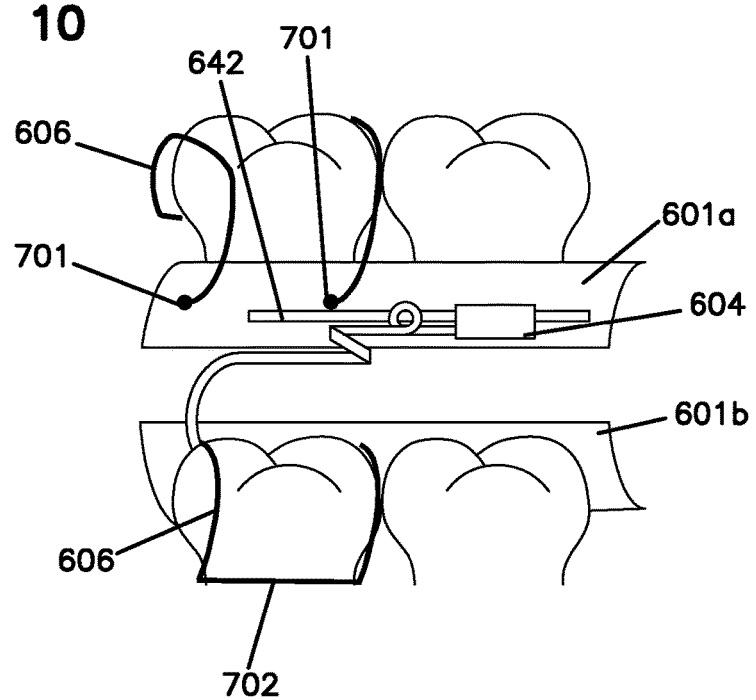

DENTAL APPLIANCE FOR CONSTRAINING THE TONGUE

CROSS REFERENCE TO RELATED APPLICATIONS

The present application is a continuation-in-part application to and claims the benefit of related PCT Application No. PCT/EP2009/060226, filed Aug. 6, 2009, and entitled "Dental Appliance for Restraining the Tongue", the disclosure of which is hereby incorporated by reference in its entirety.

This application also claims the benefit of U.S. Provisional Patent Application No. 61/086,684, filed Aug. 6, 2008, the disclosure of which is also hereby incorporated by reference in its entirety.

This application is also related to French Patent Application No. FR08-55452 entitled "Appareil dentaire de contrainte de la langue pour corriger la macroglossie et l'apnée du sommeil" filed on Aug. 6, 2008, the disclosure of which is incorporated herein by reference in its entirety.

TECHNICAL FIELD

The present disclosure relates generally to the field of dental appliances. In particular, the present disclosure relates to a dental appliance for restraining the tongue.

BACKGROUND

Orthodontic devices such as a Quad Helix are known in the art as devices that can be attached to the molars by two bands, and have four active helix springs. These orthodontic devices can correct certain pathologies such as widening the arch of the mouth to make room for crowded teeth, or correcting a posterior cross-bite, where lower teeth are buccal (outer) than upper teeth. However, these orthodontic devices do not adequately take into account the role of the tongue in the occurrence of various pathologies.

The body of the tongue, including the mobile portion, includes a pharyngeal portion and an oral portion. The pharyngeal portion represents approximately three quarters of the length of the tongue, and the oral portion represents approximately one quarter of the length of the tongue. From front to back, the oral portion includes the tip of the tongue, an anterior central zone and a posterior zone. The posterior zone is also called the dorsum of the tongue. The anterior central and posterior zones of the tongue are laterally delimited by the lateral edges of the tongue.

The tongue is an assembly of seventeen muscles. The tongue serves to remodel all the adjoining structures of the buccal cavity, including the palate, nasal fossae, jaws, and others related structures. The pharyngeal part of the tongue begins at the hyoid bone and connects to the mandible (genioglossus muscle), the skull (styloglossus muscle), and the pharynx.

Because of untimely and unceasing action, some of these muscles develop excessively. This results in the tongue having a significant volume, greater than the volume considered to be "normal," considering the size of the buccal cavity of the patient. The condition is known as large or wide tongue.

An abnormally large tongue has at its origin dysfunctions due to poor habits often acquired in childhood at an age at which the child must stop sucking and learn to chew, speak and swallow when its first teeth emerge. One form of dysfunction consists of using the tongue to form sounds other than the articulation of dental sounds (T D N and L), another dysfunction consists of sucking or aspiring saliva, a third consists of aspirating and sucking with the tongue while swallowing an alimentary bolus instead of regular swallowing. Other types of dysfunction, such as uncontrolled and disorderly movement of the tongue for speaking, swallowing chewing and resting position of the tongue are at the origin of many osseous and dental malformations and deformations such as upper and lower prognathia and labio-version (rabbit teeth, spaces between the teeth, etc.), Down's syndrome hanging tongue, backward lower jaw, protruding upper jaw, open bite between the upper and lower jaws, narrow and deep palates with mouth breathing and even loosening of the teeth.

Reflexes, if acquired incorrectly, lead to an exaggerated use of certain muscles of the oral portion of the tongue. The tongue builds muscle in a manner that is unbalanced and excessive. The tongue progressively enlarges, working back and forth, suctioning. In such cases, the patient's palate does not widen, and remains narrow and deep, going up into the nasal fossae. Respiratory problems occur because the narrow palate reduces the width of nasal fossae and their capacity. The back and forth motion of the tongue develops the genioglossus muscles at the inferior and anterior part of the mandible excessively. Buccal respiration replaces normal nasal respiration and because of its volume, the tongue can block the respiratory tracts, including the pharynx (in particular the oropharynx). The overdeveloped tongue thus serves to wrong remodelling all the adjoining structures of the buccal cavity such as the palate, nasal fossae, jaw, and other related structures, preventing or subverting development of a normal anatomy.

The resting position of the tongue is also very important. A high resting position of the tongue, stuck against the palate, results in a hollowing of the palate. A hollow palate, which is large and deep, reduces the volume of the nasal fossae and blocks the entry of the oropharynx. This may lead to reduced respiration through the nose and forced respiration through the mouth, which seems to play a role in allergic rhinitis and asthma. This is because dust (pollen, asbestos, etc.) arrives directly in the lower airways, since the air is not filtered by the nose. As with tongue dysfunctions, the tongue builds muscle in a manner that is unbalanced and excessive in this situation. Further, the tongue progressively enlarges and thickens, eventually blocking mouth respiration. Some patients may suffer both from dysfunctions and an incorrect tongue resting position.

The existing techniques for reducing the size of the tongue are essentially based on surgery. But, the results obtained by these techniques are short-lived and relapses are frequent. Among the causes of these failures is that the necessary functional reeducation after surgical intervention is difficult to achieve, since the patient continues to perform incorrect movements of the tongue reflexively even after surgery.

It is not yet widely known and accepted that wide tongue may be a main cause for OSA or snoring.

SUMMARY

In accordance with the following disclosure, the above and other issues are addressed by the following:

In a first aspect, a dental appliance includes an attachment mechanism to attach the appliance onto predetermined teeth of an upper jaw of a patient. The dental appliance also includes a constraining mechanism linked to the attachment mechanism. The constraining mechanism is positioned above a patient's tongue, and shaped to limit the movement of a posterior zone of the patient's tongue. The constraining mechanism prevents the posterior zone adhering to the palate while allowing at least an anterior zone and lateral edges of the patient's tongue to perform movements necessary for speech and swallowing.

In a second aspect, a set of dental appliances is disclosed, including the above-referenced dental appliance. The set of dental appliances also includes a further dental appliance including an attachment mechanism to attach the appliance onto predetermined teeth of an upper jaw of a patient, and a constraining mechanism linked to the attachment mechanism. The constraining mechanism of this further dental appliance is also positioned above a patient's tongue, typically at least about 2-3 millimeters above a resting position of the patient's tongue. The constraining mechanism is shaped to limit the movement of an anterior and central zone of the patient's tongue, preventing its back-and-forth motion rubbing against the palate. The constraining mechanism of this further dental appliance also allows the anterior and lateral edges of the patient's tongue to perform movements necessary for speech and swallowing.

In a third aspect, a method of treatment of an enlarged tongue is disclosed. The method includes positioning a dental appliance in a buccal cavity of a patient. The dental appliance includes an attachment mechanism to attach the appliance onto predetermined teeth of an upper jaw of a patient. The dental appliance also includes a constraining mechanism linked to the attachment mechanism, where the constraining mechanism is positioned above a patient's tongue and is shaped to limit the movement of a posterior zone of the patient's tongue, preventing the posterior zone from adhering against the patient's palate while allowing at least an anterior zone and lateral edges of the patient's tongue to perform movements necessary for speech and swallowing. The method further includes, after a first period of time, removing the dental appliance. During the first period of time, a volume of the patient's tongue is reduced, leading to normal tongue functions and less snoring or improved breathing or both.

In a fourth aspect, a dental appliance includes an attachment mechanism to attach the appliance onto predetermined teeth of an upper jaw of a patient, and a constraining mechanism linked to the attachment mechanism. The constraining mechanism is positioned above a patient's tongue and shaped to limit the movement of a anterior central zone of the patient's tongue, preventing a back-and forth motion of the tongue rubbing against the patient's palate while allowing at least an posterior zone and lateral edges of the patient's tongue to perform movements necessary for speech and swallowing. The dental appliance also includes a plurality of stems extending forwardly within the patient's mouth, positioned against an edge of the palate near palatal surfaces of teeth of an upper jaw of the patient, wherein the plurality of stems apply lateral pressure against at least the predetermined teeth, thereby widening the patient's palate.

In a fifth aspect, a method for treating an enlarged tongue in a patient is disclosed. The method includes constraining a posterior zone of the patient's tongue to limit the movement of a posterior zone, preventing it from adhering against the patient's palate while allowing at least an anterior zone and lateral edges of the patient's tongue to perform movements necessary for speech and swallowing. The method further includes continuing the constraining for a first period of time at the end of which the volume of the patient's tongue is reduced, leading to reduced snoring and improved breathing or both, and discontinuing the constraining

BRIEF DESCRIPTION OF THE DRAWINGS

FIG. 3 is a sagittal section of the buccal cavity of the patient wearing the first dental appliance of FIG. 1;

FIG. 9 is a schematic view from below of an upper jaw bearing a second embodiment of the second dental appliance; and FIG. 10 is a perspective view, from below, of a portion of the embodiment of FIG. 9.

DETAILED DESCRIPTION

Figures 1, 2:
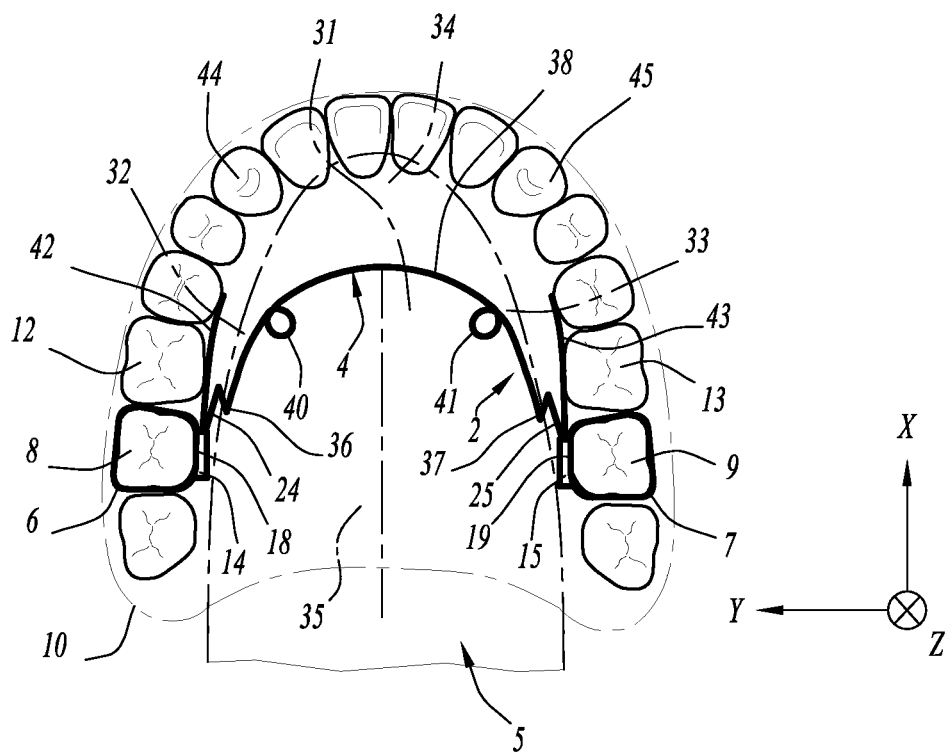
FIG. 1 is a schematic view from below of an upper jaw bearing a first dental appliance of a set of dental appliances, according to a first possible embodiment.
FIG. 2 is a schematic view from above of a lower jaw illustrating the functioning position of the first dental appliance of FIG. 1 relative to the patient's tongue.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In general, the present disclosure relates to a set of dental appliances, including a first dental appliance and a second dental appliance. These appliances can be used individually or consecutively as a set. Generally, the first dental appliance is adapted to limit the movement of an anterior zone of the body of the tongue, while allowing the remaining portions of the tongue to perform movements necessary for speech and swallowing. However, it has little influence on the resting position of the posterior part of the tongue. The second dental appliance is adapted to limit a posterior zone of the body of the tongue, while allowing the rest of the tongue to perform movements necessary for speech and swallowing. Use of one or both of these dental appliances is also discussed, in particular with respect to treatment of tongue dysfunctions, tongue abnormal resting positions and of abnormally large tongue and attendant consequences, such as sleep apnea or other respiratory irregularities.

The dental appliances of the present disclosure are described in the context of their functional position in a buccal cavity of a patient. Generally, the orientation of the figures is given by an XYZ reference frame. The x-axis corresponds to the patient's sagittal axis oriented from back to front, the y-axis corresponds to the transverse axis oriented from the patient's left to right, and the z-axis is the medial longitudinal axis, positioned substantially vertically when the patient is in the basic anatomic position, where the z-axis is oriented from bottom to top.

In some embodiments, the set of dental appliances according to this disclosure can be used in a method of treatment including the steps of placing the first dental appliance of the set on the upper jaw of a patient during a first period of time; and then, after removing the first dental appliance, placing the second dental appliance on the upper jaw of the patient during a second period of time.

Referring now to FIGS. 1-3, a first dental appliance 2 is shown, within a patient's buccal cavity 1. The first dental appliance 2 is used for constraining the tongue in a set position corresponding to a normal position for swallowing and other functions of the tongue while restraining back-and-forth movement of the anterior part of the tongue which would cause it to rub against the palate. The first dental appliance includes a forwardly-extending arch 4 shaped and positioned for contacting a patient's tongue 5. The forwardly-extending arch 4 is shaped and positioned to limit the movements of certain portions of the tongue 5, as discussed below. In the embodiment shown, attachment bands 6 and 7 retain the appliance 2 in position on the patient's upper jaw, and an additional means of support for stabilizing the appliance 2 during its use.

The first dental appliance 2 is specifically adapted for treatment of a patient condition relating to tongue dysfunctions, including patients having a deep, narrow palate. The first dental appliance 2 is configured, as discussed below, to enlarge the palate on one or both sides. First, it prevents the tongue from rubbing against the palate and it also exerts lateral pressure on the upper jaw pushing its two sides apart to enlarge the palate.

The bands, respectively right 6 and left 7, are selected in a supplier's catalog to correspond to the size of the specific teeth selected for use, and are suited for tightening on the second molars, respectively right 8 and left 9, of the patient's upper jaw 10. As a variant, the bands 6 and 7 are arranged on the first molars 12 and 13 of the upper jaw 10. For example, this arrangement can be used in the case of children in whom the second molars are not yet emerged.

Each band 6, respectively 7, is provided with a sheath or sleeve 14, 15, whose section is substantially rectangular, which for example has dimensions of 2 mm×2.5 mm and a length of order 4 mm. Such horizontal lingual sheaths are, for example, made of metal and are sold by the U.S.A. company Rocky Mountain Orthodontics with catalog number AO186. Each sheath 14, 15, is for example welded on a palatal surface 18, 19, of the band 6, 7, where the palatal surface is a surface oriented towards the inside of the buccal cavity 1. As shown in FIG. 3, the axis C of a sheath 14, respectively sheath 15, is in a substantially horizontal plane and very close to the occlusion plane P of the patient's jaws.

The arch 4 is formed from a metal wire, for example a 0.036" diameter "Elgiloy blue" type wire, sold by the American company Rocky Mountain Orthodontics, of Denver, Colo. Each of the ends 24 and 25 of the arch 4 is received in a corresponding sheath 14, 15, of the bands 6 and 7.

Seen from above, as illustrated in FIG. 2, the arch 4 is shaped to come in contact with the border 30 of the anterior central zone 31 of the patient's tongue 5, when the patient's mouth is closed so as to limit the movements of the central zone 31 of the tongue. At the same time, the right lateral edge 32, the left lateral edge 33, the forward edge or tip 34, and the posterior zone 35 of the tongue 5 can still make the movements necessary for speech or swallowing. The arch 4 follows the arch formed by the palatal surfaces of the teeth of the lower jaw 11 at a distance d which ranges between approximately 1 cm and 0.5 cm.

In certain embodiments, the arch is positioned approximately 2-3 millimeters above the normal resting position of the tongue, to restrain tongue action at the anterior central portion of the tongue 5. However, variations from this guideline are possible.

In sagittal section, as shown in FIG. 3, the arch 4 is located in the area of the plane of occlusion P. It should be noted that the arch 4 is away from the palate 3 of the buccal cavity 1 of the patient, thus preventing the tongue from rubbing against the palate.

The arch 4 comprises means of adjustment of the geometry thereof enabling an adaptation of the appliance 2 to the specific shape of the mouth of the patient.

The means of adjustment comprise predominantly vertical or slightly oblique loops 36 and 37, located on both sides of the sagittal plane and near the sheaths 14 and 15. Each vertical loop 36, 37, is made by forming a loop by winding the metal wire constituting the arch 4 on itself through 360°. Although loops 36, 37 are referred to herein as vertical loops, it is recognized that these loops can, in certain embodiments, be partially vertical (i.e. oblique or canted with respect to a vertical plane).

When the first dental appliance 2 is in functional position in the patient's mouth, the vertical loops 36 and 37 are located in a substantially vertical plane, parallel to the XZ-plane, and directed upward. The vertical loops 36 and 37 make it possible for the dental professional to elastically deform the metal wire of the arch 4 to incline the anterior section 38 of the arch 4 more or less relative to the plane of occlusion P.

The means of adjustment also comprise two substantially horizontal right 40 and left 41 loops, placed symmetrically along the anterior section 38, on both sides of the XZ sagittal plane, about 1 cm forward from each of the vertical loops 36 and 37. Although loops 40, 41 are referred to herein as horizontal loops, it is recognized that these loops can, in certain embodiments, be partially horizontal, i.e. oblique or canted with respect to a horizontal plane. The distance separating the two horizontal loops 40 and 41 varies depending on the width of the patient's buccal cavity and is generally from 2 to 3 cm. Each horizontal loop, 40 and 41, is made by forming a loop by winding the metal wire constituting the arch 4 on itself. The horizontal loops 40 and 41 enable the plastic deformation of the metallic wire constituting the arch 4 in order to adapt the shape of the arch 4 to the geometry of the patient's dentition and to the shape of the border 30 of the central zone of the tongue 5 with which the arch 4 comes in contact. Further, the horizontal loops 40 and 41 provide an additional contact surface between the arch 4 and the tongue 5 and make it possible to spread the palate if it is too narrow, and improve the nasal respiration.

The first dental appliance 2 preferably comprises an additional means of support. Actually, when the tongue 5 exerts forces on the arch 4, these forces, amplified because of the lever arm, are exerted on the bands 6 and 7, through the sheath 14 and 15. To compensate for these significant forces which tend to move the bands 6 and 7, the first dental appliance 2 is equipped with two stems, respectively right 42 and left 43, substantially straight. Each stem 42, 43, is constituted by a metal wire identical to that used for the arch 4. Each stem 42, 43, is attached at a first end to a band 6, 7, by insertion of this end in the sheath 14, 15 of this band. The stem 42, 43, extends from the sheath 14, 15, to which it is attached towards the front of the mouth 1, along the palatal surfaces of the upper jaw 10 pre-molars. The first end of the stem 42, 43, is located in the area of the first pre-molar. The stem 42, 43 comes to rest on a relief of the upper jaw 10 located at the limit between the enamel of the teeth and the gum.

As compared to related application PCT/EP2009/060226, the stems 42, 43 as shown extend forwardly within the patient's mouth one or two tooth lengths, as compared to the longer stems illustrated in that application. As such, the stems 42, 43 of the present application assist in widening a patient's palate, thereby further treating a sequela of a large tongue condition.

With this arrangement, when the sheaths 14 and 15 are subject to forces which tend to pivot them around an axis parallel to the y-axis, the stems 42 and 43 come to rest on the relief of the upper jaw, so as to generate forces which oppose the pivoting of the bands 6 and 8, while widening the palate.

For greater rigidity, in some embodiments, the first end of the stem and the end of the arch housed in the same sheath are welded together.

As a variant, a stem is made by folding the metal wire constituting the arch 4 back on itself, where the portion folded back is housed in or in any event integral with the attachment sheath.

In another variant, the arch for constraining the tongue is removable. The means for keeping the arch on the bands are consequently also adapted. For example, the palatal surface of an attachment band is provided with an element forming a sheath placed vertically, such as a Wilson 3D lingual tube with catalog number A4114 from Rocky Mountain Orthodontics of Denver, Colo., and with which combined means provided on the corresponding end of the arch engage by insertion.

As a further variant, the vertical loops are replaced by loops arranged obliquely. Such loops enable both a height and width adjustment of the arch. It is then possible to dispense with providing the arch with horizontal loops.

To position the first dental appliance 2, the dental professional tightens the bands 6 and 7 on each of the two first molars 8 and 9 of the patient's upper jaw 10. The dental professional next lodges the ends of the arch 4 and the stems 42 and 43 in the sheaths 14 and 15 and deforms them to assure the hold by tightening. Then, using pliers, the dental professional deforms the various horizontal 40 and 41 and vertical 36 and 37 loops of the arch 4 for adapting its width and height to the geometry of the patient's buccal cavity. In its functional position, the arch 4 is adjusted a little above the desired position of the tongue, which is a normal resting position in which the tongue is relaxed and located near the dental arch of the lower jaw, just behind the lower incisors, without exerting any force on them.

At the end of the adjustment, the arch 4 is such that it leaves a sheath, downward and forward, while separating from the palatal surface of the teeth in the upper jaw so as to not interfere with the occlusion. The arch 4 is deformed so as to come into contact about 0.5 cm from the outer edge of the tongue 5. The arch 4 is therefore not arranged against the patient's palate 3, but in the space between the upper and lower arches of the patient's oral cavity.

Then the stems forming the additional supports are placed along the palatal surfaces of the premolars, near the neck of the teeth, meaning in the gumline.

In alternative arrangements, bands 6 and 7 with sheaths affixed 14 and 15 can be placed on teeth other than molars 8 and 9. In one alternative embodiment, bands 6 and 7 with sheaths affixed 14, 15 can be placed on first molars 12 and 13. Preferably, due to pressure applied by the tongue 5 to the arch 4, the bands 6 and 7 with sheaths affixed 14, 15 are not placed on premolars.

Thus positioned, the appliance 2 acts by only allowing the tongue 5 the movements necessary for its normal function, meaning articulation of the alveolar sounds (T, D, N) and L, and the evacuation of the alimentary bolus and saliva by swallowing.

When the tongue 5 moves in a prohibited manner, the border 30 of the central zone meets the arch 4, which forms an obstacle. Thus, the sucking movement becomes impossible and so do other undesirable movements. To avoid injury by rubbing on the metal wire and the horizontal loop, the tongue "learns," through a reflex mechanism, to avoid certain movements and to try to remain relaxed.

Figure 4:
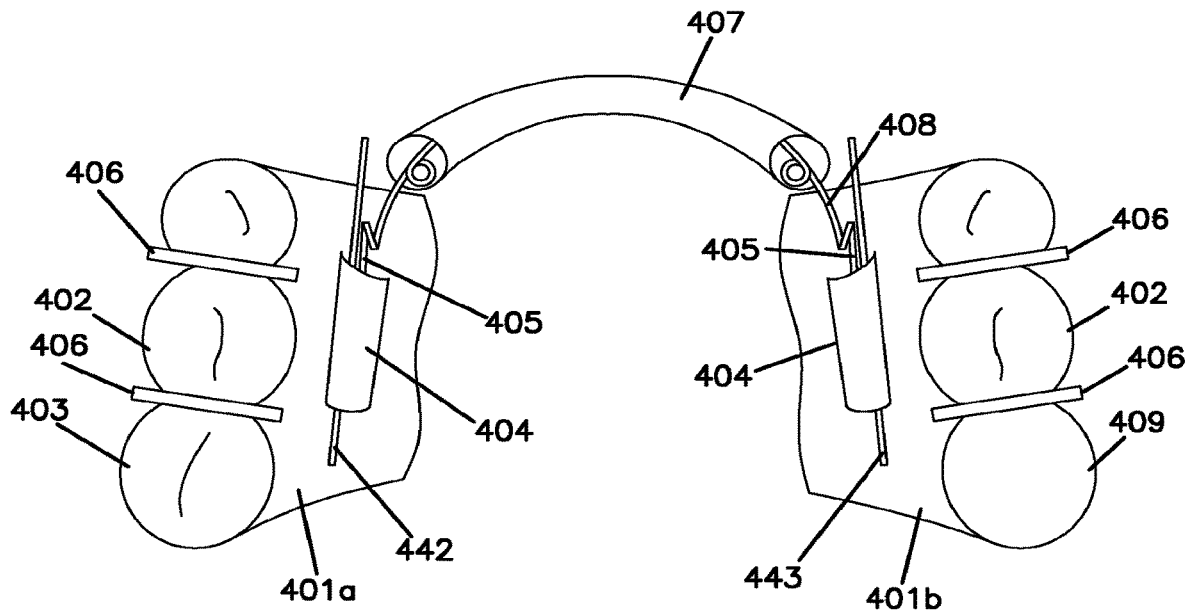
FIG. 4 is a schematic view from below of an upper jaw bearing a second possible embodiment of the first dental appliance.
Figure 5:
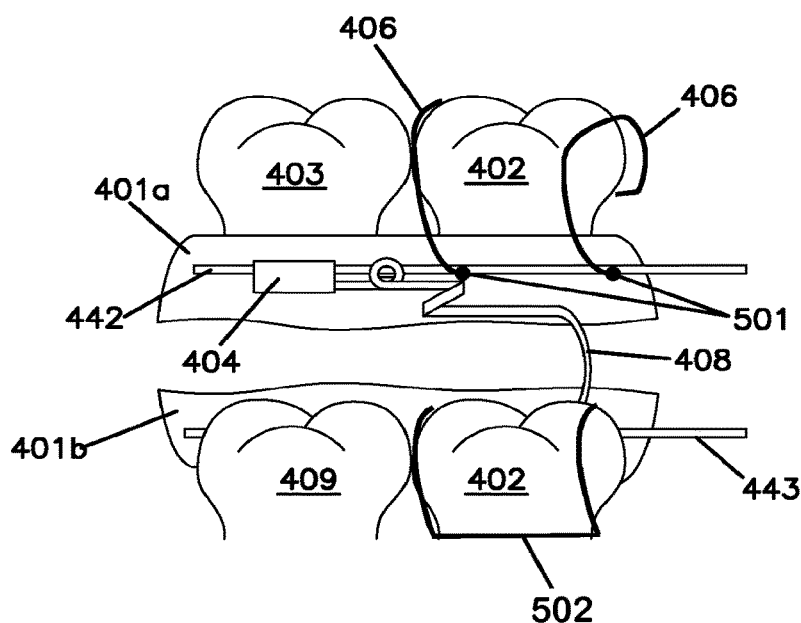
FIG. 5 is a perspective view, from below, of a portion of the embodiment of FIG. 4.

Referring to FIGS. 4-5, in another embodiment of the first dental appliance, particularly suitable for patients missing one or more molars, e.g., because of a tooth extraction, or for patients willing to remove the appliance during day time for example, the means of constraint are made by a metal wire arch set in a pair of accompanying resinous formations. Referring to FIG. 4, this embodiment includes complementary left and right resinous formations 401a-b molded to fit the patient. The resinous formations 401a-b are held in place by at least two hooks 406 on each side of the upper jaw, which grip one or more available teeth, such as teeth 402, 403. Position 409 indicates a missing tooth, and FIG. 4 illustrates hooks 406 grip the teeth that are adjacent to position 409. On the side of the teeth opposite from each respective resinous formation 401a-b, hooks 406 may be joined together by a cross-member, or may remain separate. Two sleeves 404, one on each side, are affixed by a process such as polymerization onto the resinous formations 401a-b parallel to the teeth 402, 403. The ends of the arch 405 are inserted into sleeves 404, and may be secured to sleeves 404 by a mechanical attachment such as threading, friction, or other methods known in fastening arts for this purpose. The appliance may include a sheath 407 around metal wire arch 408, the sheath 407 providing greater comfort to a user than a bare metal wire arch without a sheath.

As shown in FIG. 4, stems 442, 443 are mounted within sleeves 404 on the left and right side resinous formations 401a-b, respectively. The stems 442, 443 have analogous functions to stems 42, 43 of the first dental appliance 2, cooperating with arch 408 to widen the patient's palate.

FIG. 5 illustrates a detailed perspective view of a portion of the embodiment of FIG. 4, wherein hooks 406 are attached to resinous formations 401a-b at anchor points 501, one anchor point 501 per hook 406. Optional cross-member 502 connects two adjacent hooks 406 to provide additional stability.

In the embodiment of FIGS. 4-5, the hooks 406 are positioned to grip teeth 402, 403, which are in one embodiment first and second molars of the patient. In alternative embodiments, the hooks 406 can be positioned on resinous formations 401a-b to grip either second molars or second premolars, depending upon the geometry of the patient's mouth and the presence (or absence) or one or more teeth.

Figure 6:
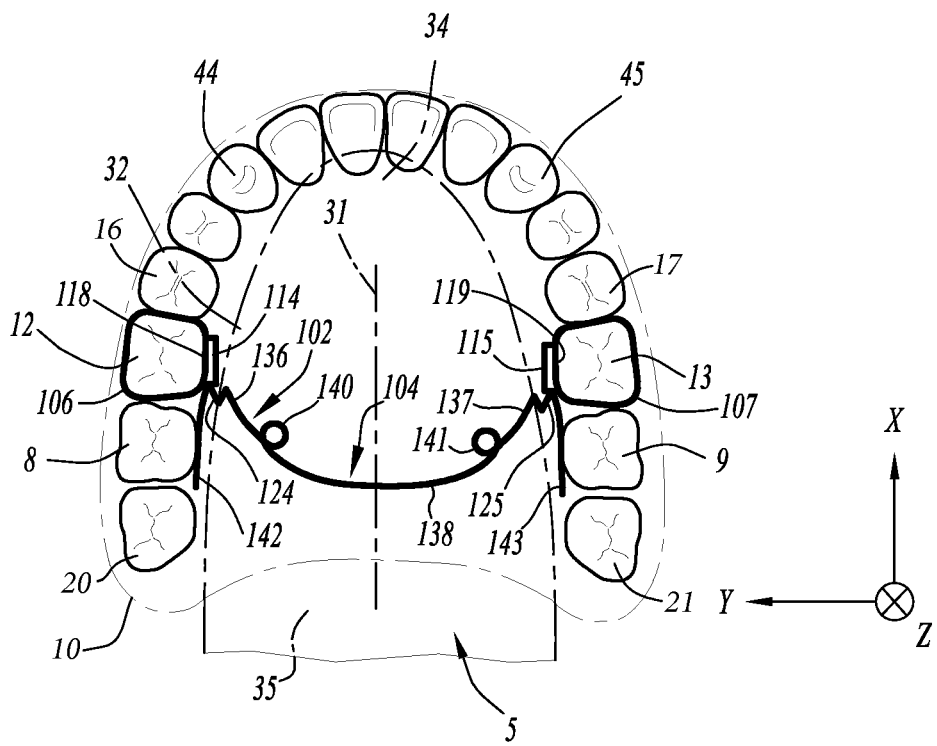
FIG. 6 is a schematic view, from below, of the upper jaw bearing a second dental appliance of the set of dental appliances, according to a possible embodiment.
Figure 7:
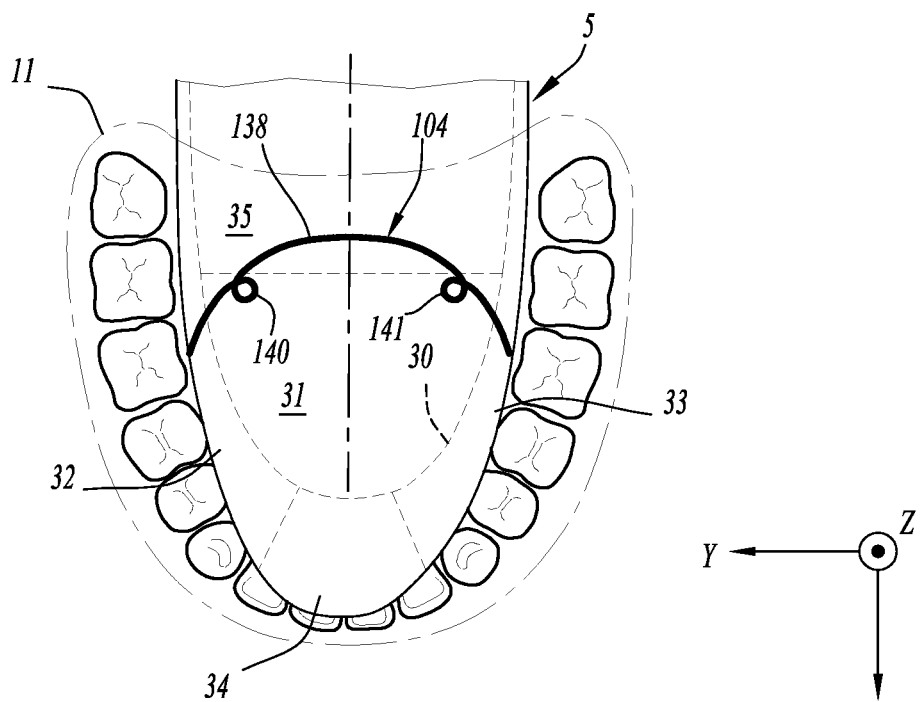
FIG. 7 is a schematic view, from above, of a lower jaw illustrating the functioning position of the second dental appliance of FIG. 6 relative to the patient's tongue.
Figure 8:
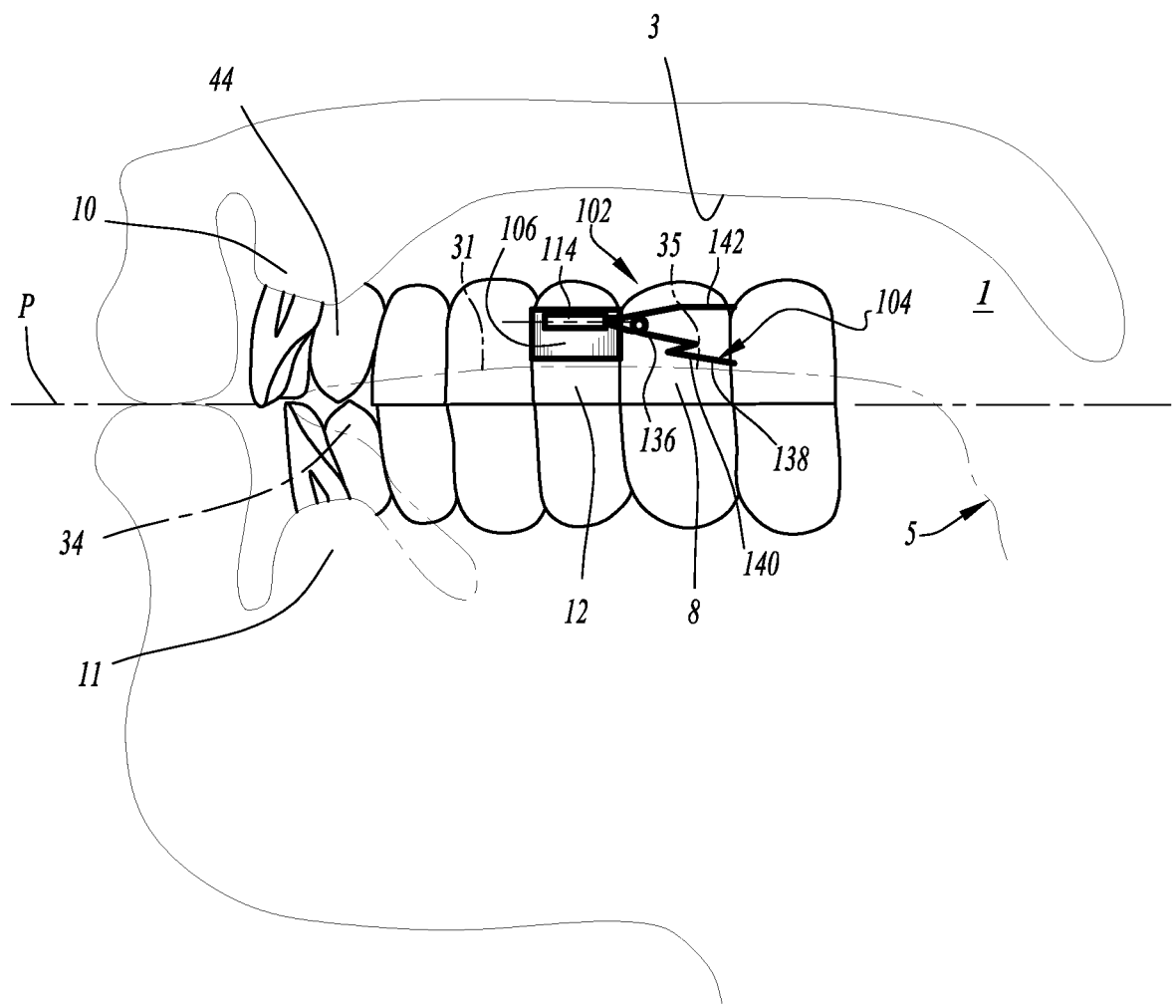
FIG. 8 is a sagittal section of the buccal cavity of the patient wearing the second dental appliance of FIG. 6.

Referring now to FIGS. 6-8, a second dental appliance 102 of a set of dental appliances is shown, within a patient's buccal cavity 1. The second dental appliance 102 is generally used for constraining the tongue 5 in a position corresponding to a normal resting position. Except where indicated or obvious for one skilled in the art, details of similar elements are as disclosed above with respect to the first dental appliance.

Generally, in comparing the second dental appliance 102 to the first dental appliance 2, while the first dental appliance 2 is constructed for restraining an anterior central zone 31 of the patient's tongue 5, the second dental appliance is constructed for restraining a posterior zone 35 of the tongue 5. The second dental appliance 102 is therefore particularly adapted for treatment of patients who have a resting position of his/her tongue 5 against the palate, but for whom palate widening is unnecessary.

The second dental appliance 102 includes an arch 104 that extends rearward within the buccal cavity 1, and is suited for contacting the patient's tongue 5 for limiting the movements thereof. Additional details regarding arch 104 are provided below.

In the embodiment shown, attachment bands 106, 107 are positioned on the first molars 12, 13, respectively, of the upper jaw 10. The attachment bands 106, 107 are configured for keeping the appliance 102 in position on the patient's upper jaw 10, and an additional means of support 142, 143 for stabilizing the appliance 102 during its use.

In alternative arrangements, the bands 106, 107 and associated sheaths 114 and 115 can be placed on teeth other than the first molars 12, 13. In one alternative embodiment, bands 106, 107 and associated sheaths 114, 115 can be placed on molars 8 and 9, for example where wisdom teeth 20, 21 are present. Preferably, due to pressure applied by the tongue 5 to the arch 4, the bands 106, 107 with sheaths 114, 115 are not placed on premolars. If sufficient teeth are not present, the embodiment described below in conjunction with FIGS. 9-10 can be used in the alternative.

In the embodiment shown, the bands 106, 107 are suited for tightening on the first molars, respectively right 12 and left 13, of the upper jaw 10. In an alternative embodiment (not shown), the attachment bands 106 and 107 are arranged on the second pre-molars 16 and 17 of the upper jaw 10. Each band 106, 107, is provided with a sheath or sleeve 114, 115, which is for example welded on a palatal surface of the band 106, 107. Each sheath 114, 115 has a substantially rectangular cross-section, and can be of varying sizes depending upon the number and size of structures to be received into the sheath. The sheaths 114, 115 can be horizontal lingual sheaths, having dimensions of approximately 2 mm×2.5 mm and a length of approximately 4 mm, as discussed above with respect to sheaths 14, 15 of FIGS. 1-3. The sheaths 114, 115 can also be welded (or otherwise affixed) on a palatal surface 118, 119 of bands 106, 107, oriented toward the inside of the buccal cavity 1. As shown in FIG. 8, the axis C of a sheath 114, respectively sheath 115, is in a substantially horizontal plane and very close to the occlusion plane P of the patient's jaws.

The arch 104 is formed from a metal wire, as explained above with respect to arch 4 of FIGS. 1-3. Each of the ends 124 and 125 of the arch 104 is received in a corresponding sheath 114, 115, of the bands 106 and 107. As shown in FIGS. 6-8, the apex of the arch 4 extends rearwardly of the band 106 and 107 within the buccal cavity 1 of the patient.

Seen from above, as illustrated in FIG. 7, the arch 104 is shaped to come into contact with the posterior central zone 35 of the patient's tongue 5, when the patient's mouth is closed so, as to limit the movements of the posterior central zone of the tongue. At the same time, the right lateral edge 32, the left lateral edge 33, the forward edge or tip 34 and the central zone 31 of the tongue 5 can still make the movements necessary for speech or swallowing.

In sagittal section, as shown in FIG. 8, the arch 104 is located in the area of the plane of occlusion P. It should be noted that the arch 104, as with arch 4 of FIGS. 1-3, is away from the palate 3 of the buccal cavity 1 of the patient. When treatment is initiated, the arch 104 can be positioned relatively closer to the palate to reduce interaction and potential pain on the tongue 5. When the tongue 5 reduces in volume due to treatment, the arch 104 can be progressively lowered toward the plane of occlusion P, to further constrain the tongue in its normal working and resting positions.

Arch 104 comprises means of adjustment of the geometry thereof, enabling an adaptation of the appliance 102 to the specific shape of the mouth of the patient. The means of adjustment comprise two substantially vertical or slightly oblique loops 136 and 137 and two substantially horizontal loops 140 and 141. As explained above, although each of these looks are referred to herein as vertical or horizontal loops, respectively, it is recognized that these loops can, in certain embodiments, be partially canted with respect to a vertical or horizontal plane, respectively.

These means enable the plastic deformation of the metallic wire constituting the arch 104 in order to adapt its shape to the geometry of the patient's dentition and to the shape of the posterior zone 35 of the tongue 5 with which the arch 104 comes into contact. Further, the horizontal loops 140 and 141 provide an additional contact surface between the arch 104 and the tongue 5.

Similarly to the first dental appliance 2, the second dental appliance 102 preferably comprises additional means of support made of two stems, respectively right 142 and left 143. The right and left stems 142 and 143, respectively, are substantially straight, and can be formed from metal wire. However, as compared to the first dental appliance 2, the stems 142, 143 of the second dental appliance 102 can in certain embodiments be further shortened, for example to a length corresponding to the width of one to one and a half teeth. The stems 142, 143 can be shortened, for example, in embodiments where the second appliance 102 is not used for enlarging the palate of a patient (e.g., the second appliance 102 is applied after treatment with the first appliance or to a patient that does not require enlarging of the palate).

The first end of each stem 142, 143, is inserted in a corresponding sheath 114, 115, alongside each end 124, 125 respectively of the arch 104. The stem 142, 143, extends from the band 106, 107, to which it is attached, towards the back of the mouth 1, along the palatal surfaces of the upper jaw molars. In the embodiment shown, the second end of the each stem 142, 143, is located in the area of the third molars 20, 21. The stems 142 and 143 come to rest on a relief of the upper jaw 10 located at the limit between the enamel of the teeth and the gum. In certain embodiments, the stems 142, 143 are approximately one tooth long, although the exact length may vary according to mouth geometry of the patient.

Additionally, each end 124 and 125 of arch 104 is received in the sheath 114, 115.

The variants encompassed for the first dental appliance 2, as discussed above, can also be applied to modify the second dental appliance 102.

In certain embodiments, the positioning of the second dental appliance 102 is done as follows.

The dental professional tightens the bands 106 and 107 on each of the two first molars 12 and 13 of the patient's upper jaw 10. The dental professional next lodges the ends of the arch 104 and the stems 142 and 143 in the sheaths 114 and 115 and deforms them to assure the hold by tightening.

Then, using pliers, the dental professional deforms the various horizontal 140 and 141 and vertical 136 and 137 loops of the arch 104 for adapting, in width and height, the geometry of the arch 104, and its posterior section 138, to the patient's oral cavity.

In its functional position, the arch 104 is such that its posterior section 138 is adjusted a little above the desired position of the tongue, which is a normal resting position in which the tongue is relaxed and located near the dental arch of the lower jaw.

At the end of the adjustment, the arch 104 is such that it leaves a sheath, downward and backward, while separating from the palatal surface of the teeth in the upper jaw so as to not interfere with the occlusion. Referring to FIGS. 6-8, the arch 104 extends from the attachment mechanism and approaches a plane of occlusion P at the apex of the arch. Referring to FIG. 8, the apex of the arch 104 is below a point where the arch extends from the attachment mechanism.

The arch 104 is deformed so as to come into contact with the tongue 5. The arch 104 is therefore not arranged against the patient's palate 3, but in the space between the upper and lower dental arches of the patient's oral cavity.

Then the stems 142, 143 forming the additional supports are placed along the palatal surfaces of the molars, near the neck of the teeth, meaning in the area of the junction of the teeth with the gums.

Thus positioned, the second dental appliance 102 acts by allowing the tongue 5 only the movements necessary for its normal function, meaning articulation of the alveolar sounds T, D, N and L, and the evacuation of the alimentary bolus and saliva by swallowing.

When the tongue 5 moves in a prohibited manner or has a bad resting position fixed on the palate, the posterior zone 35 of the tongue meets the arch 104, which forms an obstacle. To avoid injury by rubbing on the metal wire and the horizontal loops, the tongue "learns," through a reflex mechanism, to avoid certain movements and to try to remain relaxed.

Referring to FIGS. 9-10, an alternative embodiment of the second dental appliance is shown. This alternative embodiment is analogous to the embodiment of FIGS. 4-5 relating to the first dental appliance, and is particularly adaptable for patients missing one or more molars due to tooth extraction, for patients not willing to keep a dental device inserted in their mouth throughout the day, or other reasons.

In the embodiment shown, the second dental appliance 600 includes a pair of resinous formations 601a-b. In the embodiment shown, the resinous formations 601a-b are held in place by hooks 606 on each side of the upper jaw, sized and positioned to grip one or more available teeth, in the example shown teeth 602, 603. In such embodiments, the teeth 602 are engaged by the hooks 606. In alternative embodiments, the hooks 606 and resinous formations 601a-b are adapted to grip different teeth (e.g., tooth 603), for example in the case where one or both of teeth 602 are missing. In cases where other teeth are missing, one or both of the resinous formations 601a-b can be formed around the existing teeth on the left or right sides, respectively; for example, a resin formation can take a place of a missing tooth, e.g., as part of each of the resinous formations 601a-b.

As illustrated in FIG. 10, in certain embodiments, the hooks 606 are optionally joined together by a cross-member 702, which can stabilize the positions of the hooks and also assist in gripping teeth 602. However, in alternative embodiments, hooks 606 may remain separate. In the embodiment shown, the hooks 406 are attached to the resinous formations 601a-b at anchor points 501, one anchor point 501 per hook 406. Additionally, as with the device of FIGS. 4-5, the hooks 606 are positioned to grip teeth 602, 603, which are in one embodiment first molars of the patient. In alternative embodiments, the hooks 606 can be positioned on resinous formations 601a-b to grip either second molars or second premolars, depending upon the geometry of the patient's mouth and the presence (or absence) or one or more teeth.

An arch 608 is generally positioned, shaped and oriented in the same manner as arch 105 of FIG. 6-8. As with arch 408 of FIGS. 4-5, arch 608 optionally includes a sheath 607 around the metal wire of arch 608 to provide greater comfort to a user of the second dental appliance 600.

Two sleeves 604 are affixed, one on each resinous formations 601a-b, parallel to the teeth 602, 603. The sleeves 604 can be affixed to the resinous formations 601a-b by use of a polymerization process, or other equivalent methods. The ends of the arch 605 are inserted into sleeves 604, and may be secured to sleeves 604 by a mechanical attachment such as threading, friction, or other methods known in fastening arts for this purpose. The appliance may include a sheath 607 around metal wire arch 608, the sheath 607 providing greater comfort to a user than a bare metal wire arch without a sheath.

In certain embodiments, depending upon the size of the resinous formations 601a-b, sleeves 604 can be positioned on the resinous formations 601a-b, respectively, at a location adjacent to a tooth receiving hooks 606; however, in alternative embodiments, the sleeves 604 can be located further forward or backward in the mouth, for example in the case where the sleeves are adjacent to teeth 610 (or hooks are placed on teeth 610).

As shown in FIGS. 9-10, stems 642, 643 can extend from sleeves 604, and act to stabilize the dental appliance when pressure is applied on the arch 608 by a patient's tongue. As with stems 142, 143, stems 643, 643 are approximately one tooth long, although the exact length may vary according to mouth geometry of the patient.

Referring now to FIGS. 1-10 generally, during use, the first dental appliance opposes the undesirable acquired habits and hinders the dysfunction of the tongue starting from during the first days of treatment. Progressively, the tongue is re-educated so as to function properly, within the constraints of the appliance. Additionally, by stopping pressure applied by the tongue upon the palate, improved respiration through freeing the upper airways is reestablished. By forcing the tongue to move less, some muscles (e.g., the genioglossus) are less stressed and consequently, over time, their volume is reduced. By forcing the tongue to move in a proper and balanced way other muscles of the tongue regain strength and protect the capacity of the pharyngeal region. The combination of both effects enables natural breathing in the pharynx. The second appliance prevents an oversize tongue sticking to the palate and also obstructing the airways. It forces the tongue to rest in the mouth and, over time, causes it to maintain this position which in turn frees up the airways, notably the pharynx.

In about three months of treatment with the first or second appliance, a consequent reduction of the volume of the tongue is observed. To reduce the risk of relapse, an appliance is advantageously worn for about six months. If the dental professional deems necessary to remodel the shape of the palate, a dental appliance will be worn longer. For example, the positive action of the stems of the first dental appliance are emphasized by prolonged use, and act to further push apart the dental arches of the upper jaw, thus widening the palate.

Additionally, during treatment, the dental professional can modify the position of the arch of each of the first or second dental appliances, for example to further lower it towards the tongue as the volume of the tongue is reduced.

The use of the first or second dental appliance helps to improve articulation of words, because the presence of the appliance promotes the use of the lips. The first dental appliance widens the palate by pressing laterally on the teeth as the tongue presses on the arch. The palate is progressively remodeled and becomes less deep while also widening, which increases the volume of the nasal fossae and improves nasal respiration. Elimination of the sucking motion reduces the volume of the genioglossus muscle and reduces or eliminates double chin.

Since respiration is made easier, sleep apnea and snoring lessen or disappear. The patient therefore experiences deeper sleep and consequently a better quality of life, without requiring surgery. Because the first dental appliance reeducates the tongue, which models the palate, the results are more stable than these obtained with a Quad Helix.

The second appliance blocks the tongue from pressing against the palate. The tongue remains in a low and relaxed position. This also reduces the volume of the tongue and frees up the airways to make breathing easier. With the second dental appliance (e.g., dental appliance 102 or 600), the pressure exerted on the dorsum of the tongue strengthens the muscles that connect the tongue to the hyoid bone and the muscles of the pharynx wall. In addition, this increases the capacity of the airways, and straightens the spine by the action on the styloglossus. The second dental appliance is therefore adapted to the treatment of a high resting position of the tongue, where the dorsum of the tongue is in contact with the palate. After a few months, the dorsum of the tongue is flattened and the oropharynx is freed.

In some applications, the dental professional uses the first and second dental appliances as a set. For example, in certain embodiments, the first and second dental appliances are used sequentially. In a first phase of the treatment, the first dental appliance is used during a first period of time, to treat the muscles of the central zone of the tongue. After the first dental appliance has been removed, in a second phase of the treatment, the second dental appliance is used during a second period, to treat the muscles of the posterior zone of the tongue. In alternative embodiments, the treatment phases of use can be reversed, with the second dental appliance used during a first period of time and the first dental appliance used during a second period of time.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A dental appliance comprising:
an attachment mechanism adapted to attach onto a portion of an upper jaw of a patient; and
an arch linked to the attachment mechanism, the arch extending from the attachment mechanism and including an apex adapted to be positioned posterior to the attachment mechanism within a buccal cavity of the patient, wherein the arch is a metal wire that is a single piece,
wherein the arch is shaped and adapted to be positioned, above a plane of occlusion of the patient at the apex and such that the apex is below a point where the arch extends from the attachment mechanism, the apex of the arch being spaced apart from a palate of the patient, wherein opposite ends of the arch are secured at the attachment mechanism such that when the arch receives pressure by the tongue of the patient, the arch is adapted to constrain the tongue of the patient to limit movement of a posterior zone of the tongue of the patient, maintaining the posterior zone of the tongue of the patient spaced apart from the palate of the patient while allowing at least an anterior zone and lateral edges of the tongue to perform movements necessary for speech and swallowing.

2. The dental appliance of claim 1, wherein the attachment mechanism comprises a first band and a second band, the first band and the second band adapted to be located respectively on two opposite molars or premolars of the upper jaw of the patient.

3. The dental appliance of claim 2, wherein the first band and the second band are configured to be tightened on the two opposite molars.

4. The dental appliance of claim 1, further comprising first and second sleeves, the first and second sleeves receiving ends of the arch.

5. The dental appliance of claim 1, wherein the arch includes a plurality of loops.

6. The dental appliance of claim 5, wherein the plurality of loops includes at least one horizontal loop and at least one vertical loop.

7. The dental appliance of claim 6, wherein the at least one horizontal loop enables adjustment of a width of the arch, and wherein the at least one vertical loop enables adjustment of a vertical position of the arch.

8. The dental appliance of claim 1, further comprising a plurality of stems adapted to extend posteriorly within the mouth of the patient and to be positioned against an edge of the palate, and further adapted to stabilize the arch by generating forces that resist pivoting of the arch about the opposite ends of the arch when the arch receives pressure by the tongue of the patient.

9. The dental appliance of claim 1, wherein the attachment mechanism includes a plurality of resinous formations having hooks mounted thereto for engagement with the portion of the upper jaw of the patient.

10. The dental appliance of claim 9, wherein the plurality of resinous formations are adapted to at least partially reside in a location of a missing molar of the patient.

11. The dental appliance of claim 9, further comprising a plurality of sleeves mounted to the plurality of resinous formations, the plurality of sleeves receiving ends of the constraining mechanism.

12. A set of dental appliances comprising:
a first dental appliance including:
a first attachment mechanism adapted to attach onto a first portion of an upper jaw of a patient; and
a first arch linked to the first attachment mechanism, where the first arch is shaped, when worn by the patient, to limit movement of an anterior central zone of the tongue of the patient, preventing back-and-forth motion of the tongue against the palate of the patient while allowing the anterior zone and lateral edges of the tongue to perform movements necessary for speech and swallowing; and
a second dental appliance including:
a second attachment mechanism adapted to attach onto a second portion of the upper jaw of the patient; and
a second arch linked to the second attachment mechanism, the second arch extending from the second attachment mechanism and including an apex adapted to be positioned posterior to the second attachment mechanism within a buccal cavity of the patient, wherein the second arch is a metal wire that is a single piece, wherein the second arch is shaped and adapted to be positioned above a plane of occlusion of the patient at the apex and such that the apex is below a point where the second arch extends from the second attachment mechanism, the apex of the second arch being spaced apart from a palate of the patient, wherein opposite ends of the second arch are secured at the second attachment mechanism such that when the second arch receives pressure by the tongue of the patient, the second arch constrains the tongue of the patient to limit movement of a posterior zone of the tongue of the patient, maintaining the posterior zone of the tongue spaced apart from the palate of the patient, while allowing at least an anterior zone and lateral edges of the tongue to perform movements necessary for speech and swallowing.

13. A method of treatment of an enlarged tongue, the method comprising:
positioning a dental appliance in a buccal cavity of a patient, the dental appliance including:
an attachment mechanism to attach the dental appliance onto predetermined teeth of an upper jaw of the patient; and
a constraining mechanism linked to the attachment mechanism, where the constraining mechanism includes an arch extending posteriorly and positioned at a predetermined height above a plane of occlusion of the patient and is shaped to limit movement of a posterior zone of the enlarged tongue, preventing the posterior zone of the enlarged tongue from adhering against a palate of the patient while allowing at least an anterior zone and lateral edges of the enlarged tongue to perform movements necessary for speech and swallowing;
after a first period of time, removing the dental appliance;
whereby, during the first period of time, a volume of the enlarged tongue is reduced, leading to normal tongue functions and less snoring or improved breathing, or both;
positioning a first dental appliance in a buccal cavity of the patient, the first dental appliance including:
an attachment mechanism to attach the first dental appliance onto predetermined teeth of an upper jaw of the patient; and
a constraining mechanism linked to the attachment mechanism, where the constraining mechanism includes an arch extending anteriorly and positioned at a predetermined height above a plane of occlusion of the patient and shaped to limit movement of an anterior central zone of the enlarged tongue of the patient, wherein the constraining mechanism prevents a back-and-forth motion of the enlarged tongue rubbing against a palate of the patient while allowing anterior and lateral edges of the enlarged tongue to perform movements necessary for speech and swallowing;
after a second period of time, removing the first dental appliance;
whereby, during the second period of time, a volume of the enlarged tongue is reduced, leading to normal tongue functions and to less snoring or improved breathing or both.

14. The method of claim 13, wherein positioning the first dental appliance occurs prior to positioning the dental appliance, and the second period of time occurs before the first period of time.

15. The method of claim 13, whereby, during the second period of time, the palate of the patient is widened.

16. The method of claim 13, wherein the first dental appliance and the dental appliance are used sequentially.

17. The method of claim 13, wherein the first period of time comprises at least three months.

18. A method for treating an enlarged tongue in a patient, the method comprising:
attaching a dental appliance onto a portion of an upper jaw of the patient, the dental appliance including:
an attachment mechanism adapted to attach onto the predetermined teeth of the upper jaw of a patient; and
an arch linked to the attachment mechanism, the arch extending from the attachment mechanism and including an apex adapted to be positioned posterior to the attachment mechanism within a buccal cavity of the patient, wherein the arch is a metal wire that is a single piece, wherein the arch is shaped and adapted to be positioned above and approaching a plane of occlusion of the patient at the apex and such that the apex is below a point where the arch extends from the attachment mechanism, the apex of the arch being spaced apart from a palate of the patient, wherein opposite ends of the arch are secured by the attachment mechanism such that when the arch receives pressure by the enlarged tongue of the patient, the arch constrains the enlarged tongue of the patient to limit movement of a posterior zone of the enlarged tongue of the patient, maintaining the posterior zone of the enlarged tongue of the patient spaced apart from the palate of the patient while allowing at least an anterior zone and lateral edges of the enlarged tongue to perform movements necessary for speech and swallowing;
constraining, via the arch, a posterior zone of the enlarged tongue to limit the movement of the posterior zone, maintaining the enlarged tongue of the patient spaced apart from the palate of the patient while allowing at least an anterior zone and lateral edges of the enlarged tongue to perform movements necessary for speech and swallowing;
continuing the constraining for a first period of time at the end of which the volume of the patient's enlarged tongue is reduced, leading to reduced snoring and improved breathing or both; and
discontinuing the constraining.

19. The method of claim 18, further comprising:
constraining an anterior central zone of the enlarged tongue of the patient to limit the movement of the anterior central zone preventing a back-and-forth motion of the enlarged tongue rubbing against the palate while allowing the anterior and lateral edges of the enlarged tongue to perform movements necessary for speech and swallowing;
continuing the constraining for a second period of time at the end of which the volume of the patient's enlarged tongue is reduced leading to reduced snoring or improved breathing or both; and
discontinuing the constraining.

* * * * *

UNITED STATES PATENT AND TRADEMARK OFFICE
CERTIFICATE OF CORRECTION

| | |
|---|---|
| PATENT NO. | : 11,628,043 B2 |
| APPLICATION NO. | : 12/976489 |
| DATED | : April 18, 2023 |
| INVENTOR(S) | : Claude Mauclaire |

It is certified that error appears in the above-identified patent and that said Letters Patent is hereby corrected as shown below:

On the Title Page

Item (54), "CONSTRAINING" should read -- RESTRAINING --.

In the Specification

Column 1, Line 1, "CONSTRAINING" should read -- RESTRAINING --.

Signed and Sealed this
Thirtieth Day of May, 2023

Katherine Kelly Vidal
*Director of the United States Patent and Trademark Office*